United States Patent [19]

Krapf et al.

[11] 4,145,307

[45] Mar. 20, 1979

[54] MANUFACTURE OF WATER-IN-OIL EMULSIONS

[75] Inventors: Heinz Krapf, Hessheim; Knut Oppenlaender, Ludwigshafen; Karl Seib, Weinheim, all of Fed. Rep. of Germany

[73] Assignee: BASF Aktiengesellschaft, Ludwigshafen, Fed. Rep. of Germany

[21] Appl. No.: 902,909

[22] Filed: May 5, 1978

Related U.S. Application Data

[62] Division of Ser. No. 792,730, May 2, 1977, abandoned.

[30] Foreign Application Priority Data

May 22, 1976 [DE] Fed. Rep. of Germany ....... 2623085

[51] Int. Cl.$^2$ .................... B01J 13/00; C07C 89/02; C07C 91/12; C07C 91/18
[52] U.S. Cl. .................................... 252/309; 252/357; 260/584 B; 260/584 C
[58] Field of Search ...................... 252/308, 309, 357; 260/584 B, 584 C

[56] References Cited

U.S. PATENT DOCUMENTS

| 3,206,410 | 9/1965 | Moller et al. ................ 252/309 |
| 3,366,632 | 1/1968 | Wakeman et al. ............ 260/584 C X |
| 3,449,430 | 6/1969 | Dohr et al. .................... 260/584 B X |
| 3,489,690 | 1/1970 | Lachampt et al. ............ 252/308 |
| 3,499,930 | 3/1970 | Wakeman et al. ............ 260/584 C |
| 3,658,717 | 4/1972 | Graff ............................... 252/308 X |
| 3,658,718 | 4/1972 | Clumpner .................... 252/309 X |
| 3,879,464 | 4/1975 | Kalopissis et al. ........... 260/584 C |
| 4,009,255 | 2/1977 | Kalopissis et al. ........... 260/584 C X |
| 4,029,708 | 6/1977 | Seitz et al. .................... 260/584 B |
| 4,049,557 | 9/1977 | Wixon ........................... 260/584 B X |

FOREIGN PATENT DOCUMENTS

244966  5/1970  U.S.S.R. ................................ 260/584 B

OTHER PUBLICATIONS

Gallardo et al, "J. Org. Chem.", vol. 12, pp. 831–833, (1947).

*Primary Examiner*—Winston A. Douglas
*Assistant Examiner*—John Doll
*Attorney, Agent, or Firm*—Keil & Witherspoon

[57] ABSTRACT

Water-in-oil emulsifiers are obtained by reacting fatty alcohols with epichlorohydrin and reacting the resulting glycidyl ethers with amine.

6 Claims, No Drawings

MANUFACTURE OF WATER-IN-OIL EMULSIONS

This is a division, of application Ser. No. 792,730 filed May 2, 1977, now abandoned.

The present invention relates to a process for the manufacture of novel water-in-oil emulsifiers which are, above all, excellent auxiliaries for use in the cosmetics industry.

Water-in-oil emulsifiers are required in order to incorporate an aqueous phase into an oil or a fat so that these are easily spreadable (as in the case of ointments, creams, lotions or make-up). They are also required in pharmacy, in connection with the administration of active ingredients. Water-in-oil emulsifiers are also used in industry, namely in emulsion polymerization processes and in producing dispersions of polymers. Examples of water-in-oil emulsifiers used hitherto include wool grease (lanolin), lanolin alcohol derivatives, fatty acid esters of hexitols, eg. sorbitan sesquioleate, fatty acid monoglycerides, fatty acid esters of pentaerythritol, fatty alcohol citrates and fatty alcohol oxyalkylates. Finally, German Published Application No. 2,023,786 discloses, for example, the use of glycerol esters of wool wax acids as water-in-oil emulsifiers.

It is true that these water-in-oil emulsifiers are suitable for special purposes, but they frequently still suffer from disadvantages. Often, they are insufficiently stable to acids or alkalis. For example, lanolin esters and fatty acid esters are not stable to hydrolysis, and this imposes limits on their use in, for example, the cosmetics industry, since after hydrolysis the unpleasant odor of the free fatty acids manifests itself. In addition, the emulsions are often only moderately stable and the water-in-oil emulsifiers are not universally applicable to all the materials in question.

It is an object of the present invention to provide water-in-oil emulsifiers which are not only stable to all chemical factors but are also universally applicable.

Our co-pending U.S. Patent application Ser. No. 630,635 discloses a process for the manufacture of water-in-oil emulsifiers wherein saturated or unsaturated fatty alcohols of 10 to 22 carbon atoms, or their mixtures, are reacted with epichlorohydrin in the molar ratio of from 1:0.5 to 1:1.5 and the resulting glycidyl ethers are reacted with polyhydric alcohols of 2 to 6 carbon atoms, containing from 2 to 6 hydroxyl groups, or with their monoethers with fatty alcohols of 10 to 22 carbon atoms, in the molar ratio of glycidyl ether to alcohol of from 1:0.5 to 1:6.0, in the presence of acids or bases.

We have found that at least equally advantageous emulsifiers are obtained if instead of the polyhydric alcohols, compounds of the formula I

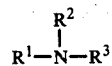

$$R^1-\underset{\underset{R^2}{|}}{N}-R^3 \qquad I$$

where $R^1$ and $R^2$ are identical or different radicals and are each hydrogen or hydroxyalkyl of 2 to 4 carbon atoms, $R^3$ is hydroxyalkyl of 2 to 4 carbon atoms or is a radical of the formula II

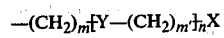

$$-(CH_2)_m\overline{[Y-(CH_2)_{m'}]_n}X \qquad II$$

in which case $R^1$ and $R^2$ must be hydrogen, Y is —O— or —NH—, m is 2 or 3, m' is 2 or 3 and may be identical to or different from m, n is from 0 to 6 and X is $NH_2$ or OH, are employed, in a molar ratio of glycidyl ether to compound of the formula I, of from 1:0.1 to 1:6.0.

Starting products for the process according to the invention include fatty alcohols and synthetic long-chain alcohols of 9 to 22 carbon atoms, eg. oleyl alcohol, stearyl alcohol, cetyl alcohol, linolenyl alcohol, myristyl alcohol, lauryl alcohol, tallow fatty alcohol and industrially manufactured alcohol mixtures, such as Alfols of 20 to 22 carbon atoms, Alfols of 16 to 18 carbon atoms, oxo-alcohols of 17 to 19 carbon atoms and oxoalcohols of 9 to 11 carbon atoms. Of course, mixtures of the alcohols, above all mixtures of the naturally occurring alcohols mentioned above, may be used.

In a first stage, the alcohols are reacted with epichlorohydrin, using a molar ratio of alcohol to epichlorohydrin of from 1:0.5 to 1:1.5, preferably of 1:1.

Examples of compounds of the formula I are monoalkanolamines, dialkanolamines and trialkanolamines, where the alkanol groups is of 2 to 4 carbon atoms, preferably monoethanolamine, diethanolamine or triethanolamine, as well as ethylenediamine, diethylenetriamine, triethylenetetramine, tetraethylenepentamine, di-n-propylenediamine and aminoethylethanolamine.

The compounds of the formula I will for simplicity be referred to below as "amines".

Acid or alkaline catalysts may be employed for the reaction of the glycidyl ethers with the amines. Examples of acid catalysts are, above all, Lewis acids such as boron fluoride etherate, boron fluoride/phosphoric acid, boron fluoride/acetic acid, boron fluoride hydrate, boron fluoride alkylglycol-etherate, tin tetrachloride, zinc chloride, titanium tetrachloride and aluminum chloride, and inorganic acids, eg. sulfuric acid; advantageous alkaline catalysts are alkali metal hydroxides, alkali metal alcoholates and alkaline earth metal alcoholates.

Of course, it is also possible to react several glycidyl ethers, mixed with one another or used successively, with the amine or with a mixture of different amines.

The reaction is advantageously carried out by first adding the acid catalyst to the amine under an inert gas at from 5° to 50° C., preferably from 20° to 30° C., and then adding the appropriate molar amount of glycidyl ether in the course of from 5 to 60 minutes, whilse maintaining a reaction temperature of from 50° to 120° C. In general, the reaction mixture is left at the chosen temperature for from 1 to 10 hours, preferably from 2 to 8 hours, whilst undergoing mechanical agitation. If, alternatively, alkaline catalysts are used, the reaction temperatures maintained are in general from 150° to 220° C., but in other respects the procedure followed is as described above. The reaction can also be carried out without a catalyst, ie. thermally. The emulsifiers manufactured according to the invention are outstandingly suitable for the manufacture of water-in-oil emulsions for the cosmetics field. Cosmetic formulations, eg. skin creams, in general contain fairly long-chain paraffins, eg. vaseline, at times also a wax component, eg. ozokerite, and also olive oil, glycerides of fatty acids, ie. fats, and preservatives, perfume oils and water. The entire system is kept in the desired state of phase distribution by means of the emulsifiers.

To manufacture water-in-oil emulsions, the procedure generally followed is to add the water, in small portions, to a fatty phase or oily phase which contains from 0.5 to 5% by weight of the emulsifier, based on the emulsion, and to stir the mixture vigorously whilst maintaining it at from 65° to 80° C. Advantageously, the water added should be at a temperature from 1° to 5° C. above that of the fatty phase or oily phase.

The emulsifiers manufactured according to the invention may be identified by data such as the density, viscosity, color number and refractive index.

The Manufacturing Examples and Use Examples which follow illustrate the invention; parts are by weight, unless expressly stated otherwise. Parts by volume bear the same relation to parts by weight as that of the milliliter to the gram.

MANUFACTURING EXAMPLES

EXAMPLE 1

61.1 parts (1.0 molar part) of monoethanolamine, 324 parts (1.0 molar part) of oleyl glycidyl ether and 1.83 parts of sodium methylate (3 percent by weight, based on amine) are heated to 175° C. under nitrogen, with vigorous stirring, and are kept at this temperature for 7 hours. A viscous liquid having very good water-in-oil emulsifier properties is obtained.

EXAMPLE 2

105.1 parts (1.0 molar part) of diethanolamine and 1.5 parts by volume of boron fluoride diethyl-etherate (49% strength) are mixed under nitrogen whilst stirring at 25° C. The mixture is heated to 65°-70° and 324 parts (1.0 molar part) of oleyl glycidyl ether are slowly added dropwise whilst ensuring that the above temperature is maintained. When all has been added, the mixture is heated to 75°-80° C. and is kept at this temperature for 5 hours. A clear liquid, which is a very good water-in-oil emulsifier, is obtained.

EXAMPLE 3

2.4 parts by volume of boron fluoride diethyl-etherate (49% strength) are added to 111.9 parts (0.75 molar part) of triethanolamine and 486 parts (1.5 molar parts) of oleyl glycidyl ether at 25° under nitrogen, whilst stirring, and the mixture is then slowly heated to 70°-75° C. It is kept at 75° C. for 7 hours and then allowed to cool, and a pale yellow clear liquid having good water-in-oil emulsifier properties is obtained.

EXAMPLE 4

30.0 parts (0.5 molar part) of ethylenediamine, 486 parts (1.5 molar parts) of oleyl glycidyl ether and 0.9 parts of sodium methylate are heated for 8 hours at 180° C. under nitrogen, with vigorous stirring. After cooling, a pale yellow liquid having very good water-in-oil emulsifier properties is obtained.

EXAMPLE 5

2.0 parts by volume of boron trifluoride/phosphoric acid (45% strength) are added to 52.1 parts (0.5 molar part) of aminoethylethanolamine under nitrogen, whilst stirring, and the mixture is heated to 65° C. At this temperature, 486 parts (1.5 molar parts) of oleyl glycidyl ether are slowly added dropwise to the reaction mixture. After completion of the addition, the temperature is raised to 100° C. and is maintained at this value for 4 hours. After cooling, a pale yellow clear liquid having excellent water-in-oil emulsifier properties is obtained.

EXAMPLE 6

154 parts (1.5 molar parts) of diethylenetriamine, 486 parts (1.5 molar parts) of oleyl glycidyl ether and 4.5 parts of sodium methylate are heated for 6 hours at 200° under nitrogen, with vigorous stirring. A liquid having good water-in-oil emulsifier properties is obtained.

EXAMPLE 7

122.2 parts (2.0 molar parts) of monoethanolamine, 162 parts (0.5 molar part) of oleyl glycidyl ether and 3.6 parts of sodium methylate are heated for 7 hours at 160° under nitrogen, whilst stirring. After removing the excess monoethanolamine, a clear pale yellow liquid having good water-in-oil emulsifier properties is obtained.

EXAMPLE 8

156.3 parts (1.5 molar parts) of aminoethylethanolamine, 966 parts (3.0 molar parts) of linoleyl glycidyl ether and 4.7 parts of sodium methylate are heated for 8 hours at 200° C. under nitrogen, whilst stirring. After cooling, a liquid having good water-in-oil emulsifier properties is obtained.

EXAMPLE 9

52.5 parts (0.5 molar part) of diethanolamine, 489 parts (1.5 molar parts) of stearyl glycidyl ether and 2.4 parts by volume of boron fluoride etherate are heated slowly to 75°-85° C. under nitrogen, whilst stirring. The above temperature is maintained for 6 hours, and a solid pale substance having water-in-oil emulsifier properties is obtained.

EXAMPLE 10

61.1 parts (1.0 molar part) of monoethanolamine, 326 parts (1.0 molar part) of an oxo-alcohol glycidyl ether (the alcohol being of 17 to 19 carbon atoms) and 2.0 parts by volume of boron fluoride etherate are heated for 7 hours at 75°-85° C. under nitrogen, whilst stirring. A colorless solid substance having water-in-oil emulsifier properties is obtained.

USE EXAMPLES

To produce an emulsion, interfacial work must be performed. As a rule, one phase is allowed to run slowly, with thorough stirring, into the other phase, at an elevated temperature (from 70° to 75° C.). The temperature of the phase being added should be about 2° C. above that of the phase initially present. In the case of water-in-oil emulsions, the water is best added in small portions to the oil/emulsifier phase. It is necessary to stir the emulsion constantly, and not too vigorously, until it is cold, and then to homogenize it. The type and duration of stirring, the control of the temperature and the mechanical system used for homogenization are essential factors.

The following is an example of the composition of a cream:

| | |
|---|---|
| Vaseline | 15.0% by weight |
| Micro-crystalline wax | 5.0% by weight |
| Olive oil | 10.0% by weight |
| Peanut oil | 10.0% by weight |
| Isopropyl myristate | 5.0% by weight |
| Emulsifier according to the invention, from Example 5 | 5.0% by weight |
| Preservative based on p-hydroxybenzoic acid esters | 0.2% by weight |
| Perfume oil | 0.3% by weight |
| H$_2$O | 49.3% by weight |

EMULSIFYING CAPACITY AND EMULSIFICATION NUMBER (WATER NUMBER)

| Emulsifiers used | Emulsifying capacity with vaseline | Emulsification number with paraffin oil | Stability of the emulsion |
|---|---|---|---|
| Emulsifier from Example 1 | 270 | 1,025 | very good |
| Emulsifier from Example 2 | 265 | 955 | very good |
| Emulsifier from Example 4 | 365 | 1,100 | very good |
| Emulsifier from Example 5 | 410 | 1,160 | very good |
| Wool wax | 140 | 600 | satisfactory |
| Fatty acid/pentaerythritol/citric acid ester | 210 | 655 | satisfactory |
| Glycerol monooleate | 190 | 730 | satisfactory |
| Sorbitan monooleate | 215 | 680 | satisfactory |
| Sorbitan sesquioleate | 230 | 815 | good |
| Sorbitan dioleate | 200 | 760 | poor |

DETERMINATION OF THE EMULSIFICATION NUMBER (WATER NUMBER)

The water number is the amount of water in g, taken up by 95 g of paraffin oil and 5 g of emulsifier. It provides information on the emulsifying capacity of water-in-oil emulsifiers. It is important not to over-interpret the results, since the water-in-oil emulsion is affected by too many other parameters to be able to make an assessment from the water number alone. The water numbers must be viewed solely as relative figures since the values obtained depend greatly on the method used.

The method here employed is as follows:

4 g of emulsifier and 76 g of paraffin oil DAB 7 are intimately mixed in a beaker by means of a magnetic stirrer, if necessary whilst warming. 20 g of this mixture, at room temperature, are introduced into the bowl of a kitchen mixer (Kenwood Chef) and homogenized for 3 minutes by means of the whisk. The rate of stirring is set to scale reading 100 by means of a regulator. It is then raised to scale reading 160 and at intervals of half a minute 1 ml of water is added at room temperature. When 20 ml of water have been taken up, the portions of water added are increased to 2 ml, and when 50 ml have been taken up they are increased to 5 ml. When the cream slips in the bowl and the water is no longer taken up in about 2 minutes, the maximum water uptake has been reached.

Since the values show a scatter of from about 5 to 10%, the water number must be determined at least 2 l or 3 times.

The water number is obtained by multiplying the grams of water taken up (determined by weighing) by a factor 5.

DETERMINATION OF THE EMULSIFYING CAPACITY

From the point of view of a reliable quick laboratory test, determination of the emulsifying capacity using vaseline as the oil phase has proved of value. 35 g of vaseline and 3 g of emulsifier are heated at 70° C. in a porcelain dish and the melt is stirred thoroughly. Water at 72° is then added in portions, whilst stirring manually with a porcelain pestle. The uptake of 62 g of water is rated as "emulsifying capacity 100". Accordingly, "emulsifying capacity 200" denotes an uptake of 124 g of water.

If all parameters are kept constant, the values show a scatter of from 5 to 10%. The values in the Table are mean values from several measurements.

The Table shows the superiority of the emulsifying capacity of the new water-in-oil emulsifiers.

STABILITY OF THE EMULSION (STABILITY OF THE CREAM)

Creams (water-in-oil emulsions) were prepared, using the water-in-oil emulsifiers according to the invention, in accordance with the instructions given below. The stability of the creams was assessed after prolonged storage at room temperature (for more than 6 months), after several weeks' test in an oven (at 40° C.) and in a refrigerator (at 6° C.) and by the "rocking" test. The Table shows that the stability of the creams manufactured using the emulsifiers of the invention is very good.

Water-in-oil cream for testing the stability:
5.0 parts by weight of emulsifier
0.2 part by weight of cetyl alcohol/stearyl alcohol
4.0 parts by weight of paraffin oil
35.8 parts by weight of vaseline
55.0 parts by weight of water
100.0

Heat stability of the emulsifiers:

Commercial water-in-oil emulsifiers and emulsifiers manufactured according to the invention were compared by storing them for 4 weeks at a low temperature and a high temperature (at 75° C. in a drying oven). The results shown in the Table below were obtained:

| | Refrigerator | Oven without $H_3PO_4$ | Oven with $H_3PO_4$ |
|---|---|---|---|
| Sorbitan sesquioleate | ++ | -- | -- |
| Glycerol/sorbitan oleic acid ester | ++ | - | -- |
| Fatty acid/pentaerythritol/citric acid ester | ++ | + | -- |
| Emulsifier from Example 1 | ++ | ++ | ++ |
| Emulsifier from Example 5 | ++ | ++ | ++ |

++ = odorless = no discoloration
+ = still odorless = at most slight yellow coloration
− = slightly rancid = from yellow to brown
− − = intolerably rancid = dark brown

We claim:

1. In a process for the production of water-in-oil emulsions at a temperature of about 65° to 80° C., wherein water is added in small portions to an oily or fatty phase containing an emulsifier, said added water having a temperature of from 1° to 5° C. above that of the fatty or oily phase, the improvement which comprises using as the emulsifier a reaction product obtained by reacting a saturated or unsaturated fatty alcohol of 9 to 22 carbon atoms, or their mixtures, with epichlorohydrin in the presence of an acid catalyst, in a molar ratio of from 1:0.5 to 1:1.5, and then reacting the resulting glycidyl ether with a compound of the formula I

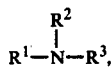

where $R^1$ and $R^2$ are identical or different radicals and are each hydrogen or hydroxyalkyl of 2 to 4 carbon atoms, $R^3$ is hydroxyalkyl of 2 to 4 carbon atoms or is a radical of the formula II

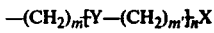

in which case $R^1$ and $R^2$ must be hydrogen, Y is —O— or —NH—, m is 2 or 3, m' is 2 or 3 and may be identical to or different from m, n is from 0 to 6 and X is $NH_2$ or OH, in a molar ratio of glycidyl ether to the compound of the formula I of from 1:0.1 to 1:6.0, in the presence of an acid or alkaline catalyst.

2. A process as claimed in claim 1, wherein oleyl alcohol, stearyl alcohol, cetyl alcohol, linolenyl alcohol, myristyl alcohol, lauryl alcohol, tallow fatty alcohol, an ALFOL of 20 to 22 carbon atoms, an ALFOL of 16 to 18 carbon atoms, an oxo-alcohol of 17 to 19 carbon atoms, an oxo-alcohol of 9 to 11 carbon atoms, or their mixtures, are employed as the saturated or unsaturated fatty alcohol.

3. A process as claimed in claim 1 wherein the fatty alcohol is reacted with epichlorohydrin in the molar ratio of 1:1.

4. A process as claimed in claim 1, wherein monoethanolamine, diethanolamine, triethanolamine, ethylenediamine, diethylenetriamine, triethylenetetramine, tetraethylenepentamine, di-n-propylamine or aminoethylethanolamine is employed as the compound of the formula I.

5. A process as claimed in claim 1, wherein boron fluoride etherate, boron fluoride/phosphoric acid, boron fluoride/acetic acid, boron fluoride hydrate, boron fluoride alkylglycol-etherate, tin tetrachloride, zinc chloride, titanium tetrachloride, aluminum chloride or sulfuric acid is employed as the acid catalyst or an alkali metal hydroxide, alkali metal alcoholate or alkaline earth metal alcoholate is employed as the alkaline catalyst.

6. A process as claimed in claim 1, wherein the reaction of the compounds of the formula I with the glycidyl ether is carried out in the presence of an acid catalyst at a reaction temperature of from 50° to 120° C. or in the presence of an alkaline catalyst at from 150° to 220° C.

* * * * *